United States Patent
Mazel (10) Patent No.: US 10,188,442 B2
(45) Date of Patent: Jan. 29, 2019

(54) CANNULATED BONE SCREW AND METHODS OF USE THEREFOF

(71) Applicant: CM DEVELOPPEMENT, Le Plessis Robinson (FR)

(72) Inventor: Christian Mazel, Le Plessis Robinson (FR)

(73) Assignee: CM DEVELOPPEMENT, Le Plessis Robinson (FR)

( * ) Notice: Subject to any disclaimer, the term of this patent is extended or adjusted under 35 U.S.C. 154(b) by 306 days.

(21) Appl. No.: 15/210,427

(22) Filed: Jul. 14, 2016

(65) Prior Publication Data

US 2018/0014867 A1 Jan. 18, 2018

(51) Int. Cl.
*A61B 17/86* (2006.01)
*A61M 5/142* (2006.01)
*A61M 25/00* (2006.01)
*A61B 17/56* (2006.01)
*A61B 17/90* (2006.01)

(52) U.S. Cl.
CPC ........ *A61B 17/864* (2013.01); *A61B 17/8605* (2013.01); *A61M 5/14276* (2013.01); *A61M 25/007* (2013.01); *A61B 2017/561* (2013.01); *A61B 2017/90* (2013.01)

(58) Field of Classification Search
CPC .................................................... A61B 17/864
See application file for complete search history.

(56) References Cited

U.S. PATENT DOCUMENTS

| 5,464,427 | A | * | 11/1995 | Curtis | ................ | A61B 17/0401 |
| | | | | | | 411/60.1 |
| 8,556,558 | B1 | * | 10/2013 | Hunt | .................... | F16B 13/141 |
| | | | | | | 411/395 |
| 9,808,337 | B2 | * | 11/2017 | Housman | ........... | A61B 17/0401 |

(Continued)

FOREIGN PATENT DOCUMENTS

EP 2 570 093 A1 3/2013

OTHER PUBLICATIONS

Mar. 14, 2017, EP communication issued for related BE application No. 201600127.

(Continued)

*Primary Examiner* — David Bates
(74) *Attorney, Agent, or Firm* — Young & Thompson (57) ABSTRACT

The present invention relates to a bone screw comprising a screw body comprising a proximal end, a distal end, a longitudinal axis and a thread along all or a portion of said screw body; a screw head; a through bore extending coaxially through said screw head and through said screw body from the proximal end up to the distal end; at least three blind channels angularly-disposed around the bore; each of said channels being configured to receive a perforated catheter or a needle; a plurality of radially-disposed fenestrations; wherein each of said channels is connected to an exterior of said screw body through at least one fenestration; and flexible directing means secured to the screw head. The present invention also relates to a system comprising such bone screw, to a method of delivering a substance to an intervertebral disc using the system according to the invention and to a method of treating vertebral tumor using the system according to the invention.

21 Claims, 4 Drawing Sheets

(56) References Cited

U.S. PATENT DOCUMENTS

| | | | | |
|---|---|---|---|---|
| 2003/0083662 | A1* | 5/2003 | Middleton | A61B 17/0401 606/323 |
| 2004/0033120 | A1* | 2/2004 | Ducker, III | F16B 33/004 411/82.1 |
| 2010/0106199 | A1* | 4/2010 | Sawa | A61B 17/7098 606/304 |
| 2011/0060240 | A1* | 3/2011 | Londot | A61B 5/053 600/547 |
| 2011/0060373 | A1 | 3/2011 | Russell et al. | |
| 2011/0282418 | A1* | 11/2011 | Saunders | A61B 17/7002 607/105 |
| 2013/0245602 | A1* | 9/2013 | Sweeney | A61B 17/7061 604/506 |
| 2014/0194886 | A1 | 7/2014 | Poulos | |
| 2014/0236242 | A1 | 8/2014 | Robinson | |
| 2014/0309691 | A1* | 10/2014 | Brown | A61L 31/06 606/232 |
| 2015/0066097 | A1* | 3/2015 | Biedermann | A61B 17/844 606/304 |

OTHER PUBLICATIONS

A. Nachemson, et al., In Vitro Diffusion of Dye Through the End-Plates and the Annulus Fibrosus of Human Lumbar Inter-Vertebral Discs, Acta Orthopaedica Scandinavica, 1970, pp. 589-607, vol. 41, Issue 6.

Michael M. Katz, et al., Intervertebral Disc Nutrition: Diffusion Versus Convection, Clinical Orthopaedics and Related Research: Section III—Basic Science and Pathology, Sep. 1986, pp. 243-245, No. 210.

J.P.G. Urban, et al., Nutrition of the Intervertebral Disc: Effect of Fluid Flow on Solute Transport, Clinical Orthopaedics and Related Research, Oct. 1982, pp. 296-302, No. 170, J. B. Lippincott Co.

Sarah E. Gullbrand, et al., Drug-Induced Changes to the Vertebral Endplate Vasculature Affect Transport into the Intervertebral Disc In Vivo, Journal of Orthopaedic Research, Dec. 2014, pp. 1694-1700, vol. 32, Issue 12, Wiley Periodicals, Inc.

J. C. Lotz, et al., The Role of the Vertebral End Plate in Low Back Pain, Global Spine Journal, 2013, pp. 153-164, vol. 3, No. 3, Georg Thieme Verlag KG, Stuttgart, New York.

Koichi Masuda, et al., New Challenges for Intervertebral Disc Treatment Using Regenerative Medicine, Tissue Engineering: Part B, 2010, pp. 147-158, vol. 16, No. 1, Mary Ann Liebert, Inc.

Franck Accadbled, et al., Influence of Location, Fluid Flow Direction, and Tissue Maturity on the Macroscopic Permeability of Vertebral End Plates, SPINE, 2008, pp. 612-619, vol. 33, No. 6, Lippincott Williams & Wilkins.

Jean-Michel Laffosse, et al., Correlations between Effective Permeability and Marrow Contact Channels Surface of Vertebral Endplates, Journal of Orthopaedic Research, Sep. 2010, pp. 1229-1234, vol. 28, Issue 9, Wiley Periodicals, Inc.

Azucena G. Rodriguez, et al., Human Disc Nucleus Properties and Vertebral Endplate Permeability, SPINE, 2011, pp. 512-520, vol. 36, No. 7, Lippincott Williams & Wilkins.

J. Wong, et al., Identification of the Compositional Traits and Permeabilities of the Cartilage Endplate that are Required for Nutrient Transport and Disc Cell Survival, Orthopaedic Research Society Annual Meeting, Mar. 19-22, 2017.

Azucena G. Rodriguez, et al., Morphology of the Human Vertebral Endplate, Journal of Orthopaedic Research, Feb. 2012, pp. 280-287, vol. 30, Issue 2, Wiley Periodicals, Inc.

* cited by examiner

CANNULATED BONE SCREW AND METHODS OF USE THEREFOF

FIELD OF INVENTION

The present invention pertains to the field of bone screws. In particular, the invention relates to cannulated bone screws and methods of use thereof for the treatment of bone.

BACKGROUND OF INVENTION

Delivery of drugs or therapeutics to bones is an often desirable but difficult to achieve process, especially if one desire to focus the delivery to the interior of a bone or to a particular area in a bone.

US 2014/0236242 teaches to use a screw for bone fixation comprising an elongate shank defining an internal longitudinal passage and at least one shank aperture in communication with the internal longitudinal passage. However with such device, the discharge of substances within the bone is mainly distal due to the distal opening required to insert a guiding wire. Such guiding wire is necessary for minimally invasive surgery. Minimally invasive surgery, which is applied to an increasing number of cases, required indeed guiding wires to position an implant to the implantation site.

EP 2570093 suggests inserting a plug member into the internal longitudinal passage to close the passage at the distal end after removal of the guiding wire. Such system enables radial ejection of substance by preventing distal discharge of fluid. However, insertion of the plug member required complex handling.

It is thus a first object of the invention to provide a bone screw enabling discharge of substances in an oriented manner while allowing minimally invasive surgery.

The object is solved by the device as defined in the claims. The present invention especially provides a bone screw having a longitudinal axis, a through bore extending coaxially and at least three blind channels angularly-disposed around the through bore. Each blind channel is connected to the exterior of the bone screw by fenestrations. With such device, the discharge of substances may be oriented by selecting the desired blind channel.

Orienting the delivery of substance within the bone may be of importance, especially for treating the intervertebral disc. Intervertebral disc has indeed no specific vascularization. Avascular tissue nutrients are delivered by diffusion from the capillaries at the disc-vertebral body interface. Consequently, intravenous treatments have difficulties to access intervertebral disc. The state of the art procedure requires disc puncture and perforation of the disc annulus. However, such procedure often leads to degenerative disc disease.

It is consequently a second object of the invention to enable treatment of the intervertebral disc without puncture of the disc annulus.

The cannulated bone screw according to the invention has the advantage that it can deliver substance inside the vertebral body precisely towards the superior or inferior end plate; such substances being subsequently diffused inside respectively the superior or inferior intervertebral disc.

Alternatively, the cannulated bone screw according to the invention may also be used with radioactive needles positioned in the blind channels, thereby providing local radiotherapy within the bone.

After the implant is inserted into the vertebral body, a catheter, inserted in a blind channel, may be connected to a pump implanted just below the surface of the skin. The patient may thereby keep the system for several hours to several days. Once the treatment is achieved, in order to access the bone screw percutaneously, it is necessary that extracting means locate the head screw easily.

It is thus a third object of the invention to provide a bone screw enabling removal by minimally invasive surgery.

The object is solved by the device as defined in the claims. In particular, the present invention provides flexible directing means secured to the screw head such that extracting means may be guided to the screw head. As the directing means are secured to the screw head, the extracting means may slide around said directing means until it abuts against the screw head for retrieval.

SUMMARY

The present invention relates to a bone screw comprising:
- a screw body comprising a proximal end, a distal end, a longitudinal axis and a thread along all or a portion of said screw body;
- a screw head attached to the proximal end of the screw body;
- a through bore extending coaxially through said screw head and through said screw body from the proximal end up to the distal end;
- at least three blind channels angularly-disposed around the through bore; said channels extending longitudinally through said screw head and through a portion of said screw body; and each of said blind channels being configured to receive a catheter or a needle;
- a plurality of radially-disposed fenestrations; wherein each of said blind channels is connected to an exterior of said screw body through at least one fenestration; and
- flexible directing means secured to the screw head such that extracting means may be guided to the screw head along said means.

In one embodiment, the at least three blind channels are regularly angularly-disposed. In one embodiment, the bone screw comprises four blind channels disposed at every 90°.

In one embodiment, at least one of the blind channels has a different length than the other channels.

In one embodiment, the fenestrations are elongated holes. In one embodiment, a fenestration is located at the distal end of each blind channel. In one embodiment, the at least one fenestration connecting each blind channel to an exterior of the screw body are not positioned in the same transverse plane. In one embodiment, the fenestrations are positioned between the crests of adjacent thread.

In one embodiment, the bone screw further comprises a radiopaque marker (or radioopacifier) enabling positioning, especially angular positioning, of the bone screw within the bone.

In one embodiment, the flexible directing means are a wire, preferably a braided wire, more preferably a metallic braided wire. In one embodiment, the flexible directing means is hollow and configured to receive at least one catheter or at least one needle According to said embodiment, the flexible directing means may be a braided sleeve, preferably a metallic braided sleeve; or a coiled sleeve, preferably an elastic or metallic coiled sleeve.

In one embodiment, the lead of the thread varies along the screw body. In one embodiment, the lead of the thread is larger in the distal portion of the screw body than in the proximal portion of the screw body.

The present invention also relates to a system comprising a bone screw according to the present invention and at least one catheter, such as for example a perforated catheter, or at least one needle, such as for example a radioactive needle.

In one embodiment, the system further comprises a stopper comprising an opening for each catheter or each needle and for guiding means; said stopper being configured to be inserted in the screw head in a tight manner.

In one embodiment, the system further comprises a subcutaneous fluid pump fluidly connected to the catheter.

The present invention further relates to a method of delivering a substance to an intervertebral disc; said method comprises the following steps:

implanting via transpedicular approach at least one system comprising:
- a bone screw comprising
  - a screw body comprising a proximal end, a distal end, a longitudinal axis and a thread along all or a portion of said screw body;
  - a screw head attached to the proximal end of the screw body;
  - a through bore extending coaxially through said screw head and through said screw body from the proximal end up to the distal end;
  - at least three blind channels angularly-disposed around the through bore; said channels extending longitudinally through said screw head and through a portion of said screw body; and each of said blind channels being configured to receive a catheter or a needle;
  - a plurality of radially-disposed fenestrations; wherein each of said blind channels is connected to an exterior of said screw body through at least one fenestration; and
  - flexible directing means secured to the screw head such that extracting means may be guided to the screw head; and
- at least three perforated catheters, wherein each bind channel comprises a perforated catheter.

selecting the catheter which is in the blind channel directed towards the superior or the inferior end plate; and
delivering a substance within the selected catheter such that the substance diffuses towards respectively the superior or the inferior intervertebral disc.

In one embodiment, the method further comprises the step of implanting a fluid pump fluidly connected to the selected catheter subcutaneously.

In one embodiment, the method further comprises the step of guiding extracting means along the flexible directing means to the screw head and extracting the bone screw and the at least three catheters.

The present invention further relates to a method of treating vertebral tumor; said method comprises the following steps:

implanting via transpedicular approach at least one system comprising:
- a bone screw comprising
  - a screw body comprising a proximal end, a distal end, a longitudinal axis and a thread along all or a portion of said screw body;
  - a screw head attached to the proximal end of the screw body;
  - a through bore extending coaxially through said screw head and through said screw body from the proximal end up to the distal end;
  - at least three blind channels angularly disposed around the through bore; said channels extending longitudinally through said screw head and through a portion of said screw body; and each of said blind channels being configured to receive a perforated catheter or a needle;
  - a plurality of radially-disposed fenestrations; wherein each of said blind channels is connected to an exterior of said screw body through at least one fenestration; and
  - flexible directing means secured to the screw head such that extracting means may be guided to the screw head; and
- at least one radioactive needle positioned in at least one blind channel;

irradiating the vertebra; and
guiding extracting means along the flexible directing means to the screw head and extracting the bone screw and the at least one needle.

DEFINITIONS

In the present invention, the following terms have the following meanings:

The term "about" is used herein to mean approximately, roughly, around, or in the region of When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

"Distal" refers to the direction toward which the bone screw is advanced as the bone screw is engaged to bone and "proximal" refers to the direction opposite the distal direction.

"Flexible" refers to the ability of an object to deform in a reversible manner.

"Longitudinally" means extending in the direction of the length of a material.

"Substance" refers to one or more chemical compounds that are useful when delivered to the vicinity of a bone, preferably to the vicinity of a vertebra or to the vicinity of an intervertebral disc. Substances may be chosen to help treat diseased bone or joint. Representative example substances include drugs or therapeutics such as anti-inflammatory drugs, anesthetics, antibiotics, chemotherapeutics, interleukin, bone morphogenetic proteins, bone growth factors or disc nutrients. Within the present invention, substance may be a liquid or a gel.

"Therapeutically effective amount" means level or amount of agent that is aimed at, without causing significant negative or adverse side effects to the target, (1) delaying or preventing the onset of a disease; (2) slowing down or stopping the progression, aggravation, or deterioration of one or more symptoms of the disease; (3) bringing about ameliorations of the symptoms of the disease; (4) reducing the severity or incidence of the disease; or (5) curing the disease. A therapeutically effective amount may be administered prior to the onset of the disease, for a prophylactic or preventive action. Alternatively or additionally, the therapeutically effective amount may be administered after initiation of the disease, for a therapeutic action.

Within the present invention, a "through bore" is a bore that goes all the way through the material. This is to distinguish it from a "blind channel", which does not go all the way through the material of the object.

"Transverse plane" refers to a plane perpendicular to the longitudinal axis of the screw body.

DETAILED DESCRIPTION

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly it should be understood that where features mentioned in the appended claims are followed by reference signs, such signs are included solely for the purpose of enhancing the intelligibility of the claims and are in no way limiting on the scope of the claims.

Figure 1:
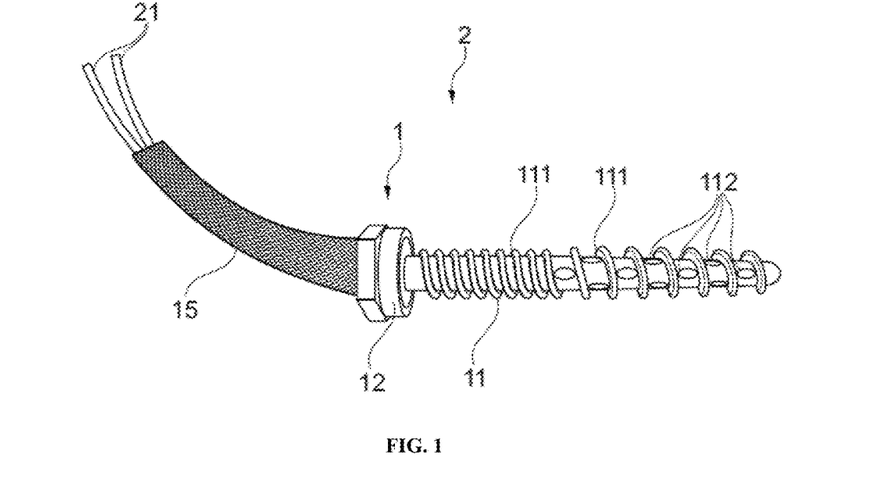
FIG. 1 shows the system comprising two catheters according to the invention.
Figure 2:
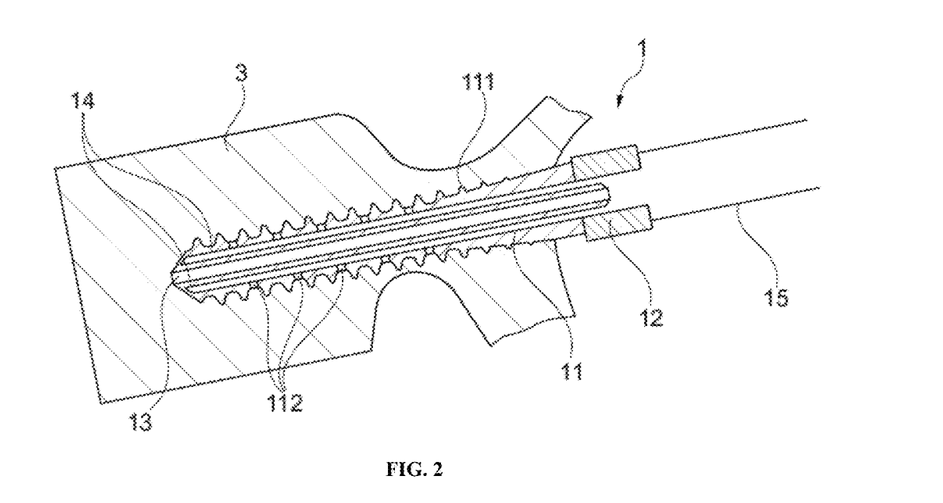
FIG. 2 is a sectional view of a bone screw according to the present invention in a vertebra.

FIGS. 1 to 9 show a bone screw or a system comprising the bone screw according to the invention. As depicted in FIG. 2, the bone screw 1 comprises a screw body 11 for anchoring in the bone, e.g. a vertebra 3. Said screw body 11 comprises a proximal end, a distal end which may be shaped as a tip, a longitudinal axis and a thread 111 along all or a portion of said screw body 11. Said thread 111 is located along all or a portion of the exterior of the screw body 11. The bone screw 1 further comprises a screw head 12 attached to the proximal end of the screw body 11. The screw head 12 may be any screw head comprising engagement structure, e.g. a hexagonal screw head as depicted in FIG. 1, for engagement with a tool, e.g. inserting means and extracting means. In one embodiment, the screw head 12 is integral with the screw body. In one embodiment, the screw body 11 has a length ranging from 35 to 55 mm. In one embodiment, as depicted in FIG. 2, the screw body 11 is substantially cylindrical and the diameter of the screw body 11 is ranging from 5.5 mm to 6.5 mm, preferably about 6 mm.

The material from which the bone screw 1, especially the screw body 11 and the screw head 12 is made, can be any material which is usual for bone screws. In one embodiment, said material is titanium, titanium alloy such as nitinol, stainless steel or any biocompatible metal alloy. In another embodiment, said material is a biocompatible plastic, such as PEEK.

According to one embodiment, the lead of the thread 111 varies along the screw body 11. According to one embodiment, the lead of the thread 111 is larger in the distal portion of the screw body 11 than in the proximal portion of the screw body 11. Said embodiment may improve anchorage of the bone screw within the pedicle of a vertebra.

Figures 3A, 3B:
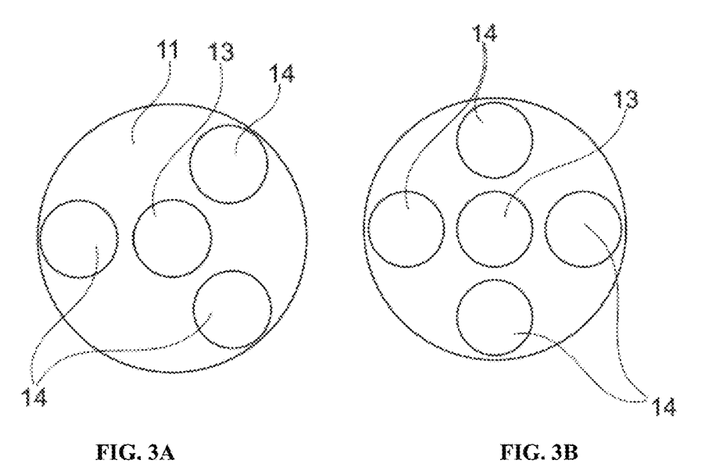
FIG. 3A is sectional view of the screw body in a transverse plane wherein the bone screw comprises three blind channels.
FIG. 3B is sectional view of the screw body in a transverse plane wherein the bone screw comprises four blind channels.

The bone screw 1 is cannulated. As shown in FIGS. 2, 3A and 3B, it comprises a through bore 13 extending coaxially through said screw head 12 and through said screw body 11 from the proximal end up to the distal end. The diameter of the bore 13, and especially of the portion of the bore extending within the screw body 11, is designed such that guiding means 22 (see FIG. 7B), commonly used for minimally invasive surgery, can be guided through the bone screw 1. In one embodiment, the diameter of the bore 13 is ranging from 0.8 mm to 2.8 mm, preferably about 1.8 mm.

As shown in FIGS. 2, 3A, 3B and 9, the bone screw 1 further comprises at least three blind channels 14 angularly (i.e. peripherally) disposed (or positioned) around the through bore 13. Said blind channels 14 extend longitudinally (i.e. parallel to the longitudinal axis of the screw body 11) through said screw head 12 and through a portion of said screw body 11. According to one embodiment, said blind channels 14 are regularly disposed around the through bore 13. According to one embodiment, as depicted in FIG. 3A, the bone screw 1 comprises three blind channels 14, preferably three blind channels equally spaced around the through bore 13, i.e. at every 120°. According to one embodiment, as depicted in FIG. 3B, the bone screw 1 comprises four blind channels 14, preferably four blind channels equally spaced around the through bore 13, i.e. at every 90°. As it is apparent to one skilled in the art, the bone screw may comprises as many blind channel as required to the skilled artisan, e.g. 3, 4, 5, 6, 7 or 8 blind channels. The blind channels 14 are not fluidly connected to the through bore 13 within the screw body 11.

In one embodiment, each blind channel 14 has the same diameter. The diameter of the blind channels 14, and especially of the portion of the blind channel 14 extending within the screw body 11, is designed such that a catheter or a needle can be guided therethrough. In one embodiment, the diameter of the blind channels 14 is ranging from 0.5 mm and 2.5 mm, preferably about 1.5 mm. In one embodiment, each of said blind channels 14 is configured to receive at least partially a catheter or a needle.

According to one embodiment, at least one of the blind channels 14 has a different length than the other channels. Said embodiment ensures that substances are delivered at a particular location along the screw body 11 depending of the blind channel 14. According to one embodiment, each of the blind channels 14 has a different length.

As depicted in FIGS. 1, 2, 4, 5 and 6, the bone screw further comprises a plurality of radially-disposed fenestrations 112. A fenestration 112 connects a blind channel 14 to an exterior of said screw body 11. In one embodiment, the bone screw 1 comprises as many fenestrations 112 as blind channels 14. In another embodiment, the bone screw 1 comprises more than one fenestration 112 for each blind channel 14. In one embodiment, the fenestrations 112 are radially-disposed from the blind channels 14 to the exterior of the screw body 11.

According to one embodiment, the fenestrations 112 are circular. According to a preferred embodiment, the fenestrations 112 are elongated holes. Such embodiment maximizes the surface of the hole and prevents clogging due to healing once the bone screw is inserted into the bone.

According to one embodiment, the elongated holes have an elliptic shape. In one embodiment, the minor axis of the elliptical hole is orthogonal to the longitudinal axis of the bone screw and has a length inferior to a quarter of the perimeter of the screw body 11 measured in a transverse plane. Such embodiment prevents that a fenestration 112 overlaps two blind channels. In one embodiment, the minor axis has a length equal to a fifth, a sixth, a seventh or a eighth of the perimeter of the screw body 11. In one embodiment, the major axis of the elliptical hole is parallel to the longitudinal axis of the bone screw 1 and has a length equals to at least twice or at least thrice the length of the minor axis.

According to one embodiment, a fenestration 112 is located at the distal end of each blind channel 14.

According to one embodiment wherein the bone screw 1 is intended to be inserted into a vertebra 3, the fenestrations 112 are located on the distal portion of the screw body 11 such that substances may be discharged within the vertebral body and not within the pedicle. According to one embodiment, the fenestrations 112 are not located on the proximal portion of the screw body 11. In one embodiment, the length of the proximal portion of the screw body 11 is about 15 mm.

According to one embodiment, the fenestrations 112 connecting each blind channel 14 to an exterior of the screw body 11 are not positioned in the same transverse plane. According to one embodiment, the fenestrations 112 connecting adjacent blind channels 14 to an exterior of the screw body 11 are not positioned in the same transverse plane. Said embodiments ensure that substances are delivered at a particular location along the length of the screw body 11 depending of the blind channel 14. Said embodiments also strengthen the mechanical design of the bone screw 1.

According to one embodiment, as shown in FIG. 1, the fenestrations 112 are positioned between the crests of adjacent thread.

Figure 7A:
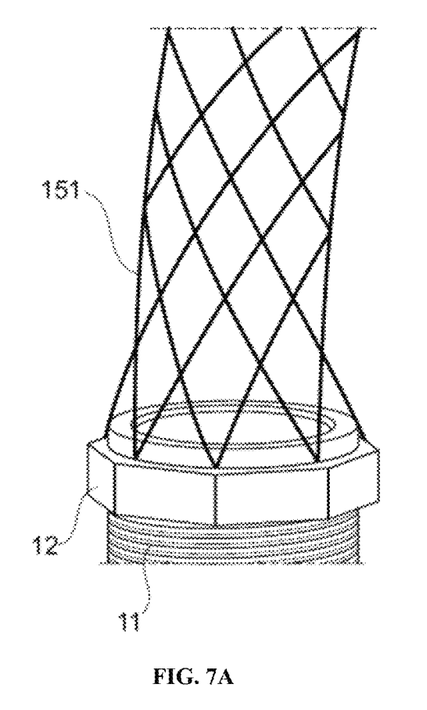
FIG. 7A is a partial front view of the bone screw according to the present invention.

The bone screw further comprises flexible directing means 15 secured to the screw head 12 such that extracting means may be guided to the screw head 12. In one embodiment, as shown in FIG. 7A, the flexible directing means 15 are secured about a proximal end of the screw head 12. The flexible directing means 15 may be secured to the screw head 12 by any means known to one skilled in the art such as for instance gluing, welding or screwing. According to one embodiment, the flexible directing means 15 have a length ranging from 10 to 15 cm, preferably about 12 cm.

Figure 4:
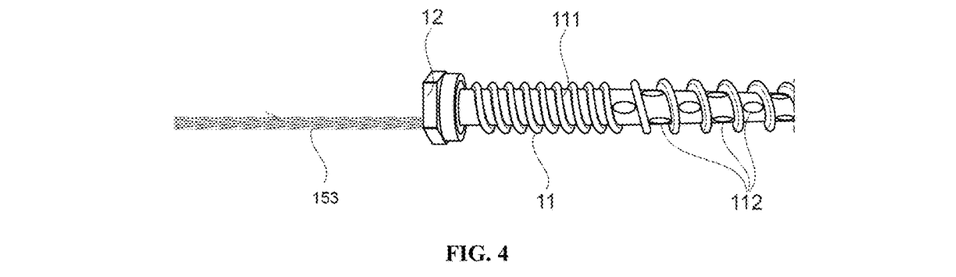
FIG. 4 is a partial side view of the bone screw according to the present invention wherein the flexible directing means are a braided wire.

According to one embodiment, as depicted in FIG. 4, the flexible directing means 15 are a flexible wire 153, preferably a flexible braided wire, more preferably a flexible metallic braided wire.

Figure 5:
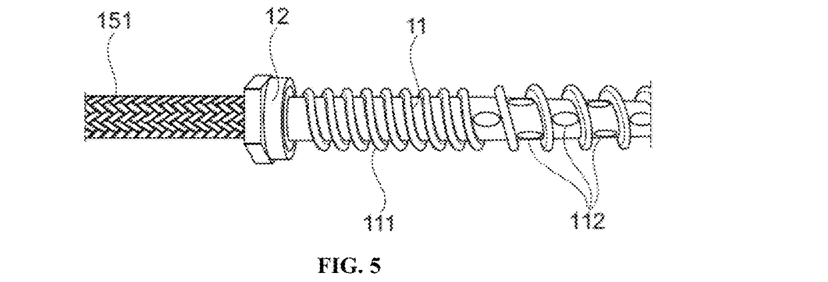
FIG. 5 is a partial side view of the bone screw according to the present invention wherein the flexible directing means are a braided sleeve.
Figure 6:
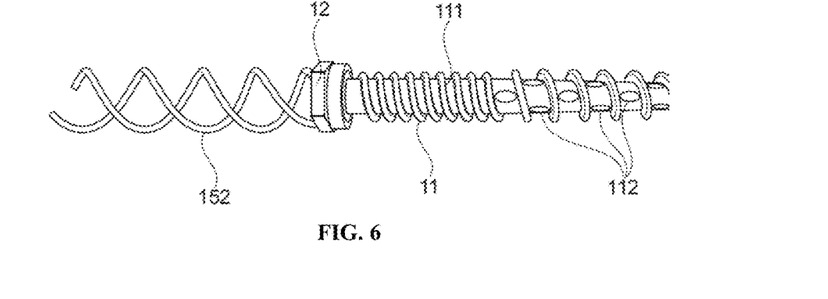
FIG. 6 is a partial side view of the bone screw according to the present invention wherein the flexible directing means are a coiled sleeve.
Figure 7B:
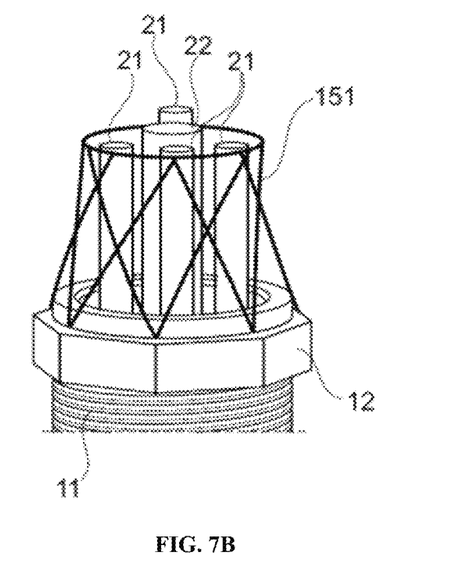
FIG. 7B is a partial front view of the system comprising four catheters and guiding means according to the present invention.

According to alternative embodiments, the directing means 15 are hollow and configured to receive at least partially at least one catheter or at least one needle, as depicted in FIGS. 5 and 6. According to one embodiment, as depicted in FIG. 7B, the hollow flexible directing means 15 is configured to receive guiding means 22 and as many catheter or needle as the number of blind channels 14. According to one embodiment, the hollow flexible directing means 15 are a sleeve, preferably a cylindrical sleeve. According to one embodiment, as shown in FIG. 5, the hollow flexible directing means 15 comprises a braided sleeve 151, preferably a metallic braided sleeve. According to another embodiment, as shown in FIG. 6, the hollow flexible directing means comprises a coiled sleeve 152, preferably an elastic or metallic coiled sleeve.

According to one embodiment, the bone screw 1 further comprises a radiopaque marker (not represented) enabling positioning, especially angular positioning, of the bone screw within the bone. Said embodiment enables the surgeon to choose the blind channel to deliver a substance in the chosen direction.

The present invention also relates to a system 2 comprising a bone screw 1 according to the present invention.

As depicted in FIG. 1, the system 2 comprises a bone screw 1 comprising:
- a screw body 11 comprising a proximal end, a distal end, a longitudinal axis and a thread 111 along all or a portion of said screw body;
- a screw head 12 attached to the proximal end of the screw body 11;
- a through bore extending coaxially through said screw head 12 and through said screw body 11 from the proximal end up to the distal end;
- at least three blind channels angularly-disposed around the through bore; said channels extending longitudinally through said screw head 12 and through a portion of said screw body 11; and each of said blind channels being configured to receive a catheter 21 or a needle;
- a plurality of radially-disposed fenestrations 112; wherein each of said blind channels is connected to an exterior of said screw body 11 through at least one fenestration 112; and
- flexible directing means 15 secured to the screw head 12 such that extracting means may be guided to the screw head along said means; and
- at least one catheter 21, preferably a perforated catheter.

The system 2 comprises a bone screw 1 and at least one catheter 21, such as a perforated catheter 21, or at least one needle, such as a radioactive needle. In one embodiment, the catheter 21 is perforated on its distal portion such that when the catheter 21 abuts the distal end of a blind channel 14, substances are discharged only in the screw body 11. In one embodiment, the system 2 comprises only one catheter 21 or needle. In one embodiment, the system 2 comprises only two catheters 21 or needles. In another embodiment, the system 2 comprises a needle or a catheter 21 in each blind channel 14.

According to one embodiment, the system 2 further comprises guiding means 22.

According to one embodiment, the system 2 further comprises a stopper 23. Said stopper 23 is configured to be inserted in the screw head 12 in a tight manner. In one embodiment, the stopper 23 comprises on its perimeter an O-ring 231 ensuring tightness between the stopper 23 and the screw head 12.

According to one embodiment, the stopper 23 comprises an opening for each catheter 21 or each needle. Said openings are sized to ensure tightness between the opening and the catheter 21 or needle. Said openings comprise optionally an O-ring.

Figure 8:
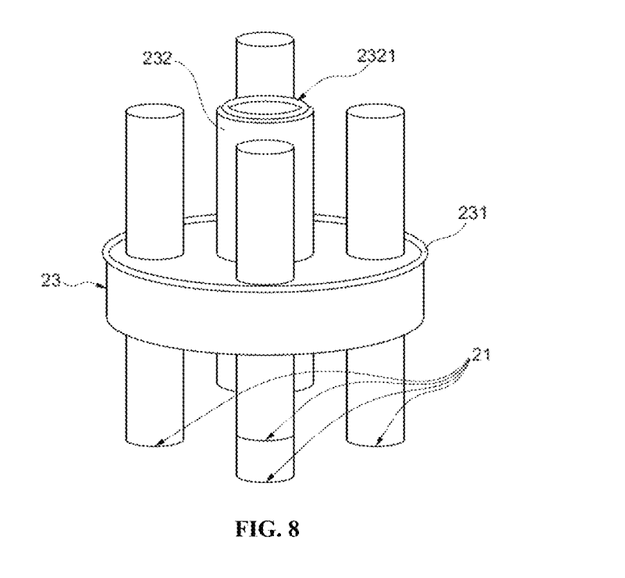
FIG. 8 illustrates the stopper according to the present invention.
Figure 9:
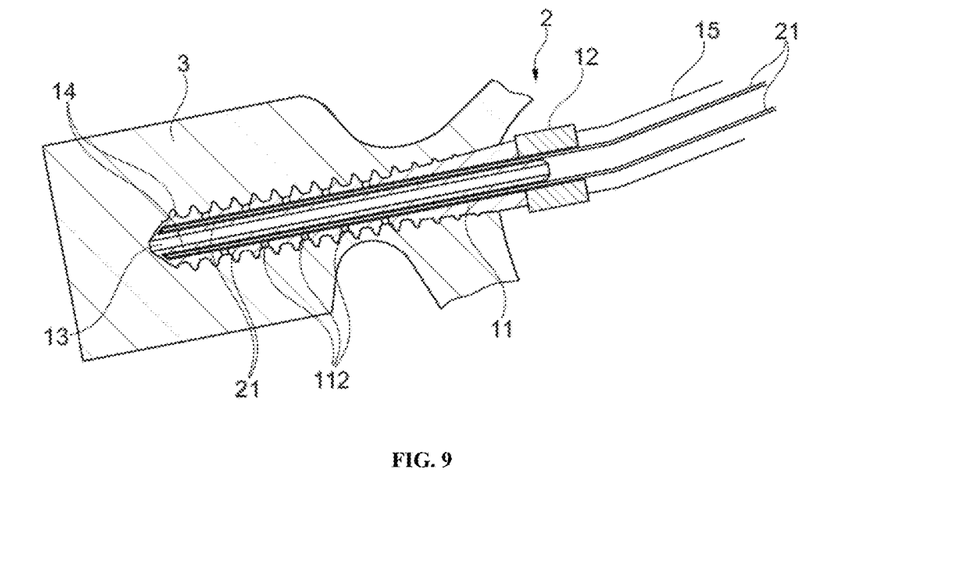
FIG. 9 is a sectional view of a system comprising at least two catheters according to the present invention in a vertebra.

According to one embodiment, the stopper 23 comprises an opening for the guiding means 22. Said opening is sized to ensure tightness between the guiding means 22 and the stopper 23. In one embodiment, said opening comprise an O-ring. In one alternative embodiment, as depicted in FIG. 8, the stopper 23 comprises a guiding tube 232 connected to the stopper 23 in a tight manner. Said guiding tube 232 is configured to receive the guiding means 22 in a tight manner. In one embodiment, said guiding tube 232 comprises an O-ring 2321 to ensure tightness between the guiding means 22 and the guiding tube 232.

The stopper 23 according to the present invention prevents backflow from the blind channels 14 and exchanges of substances between the blind channels 14 through the screw head 12.

According to tone embodiment, the system 2 further comprises a subcutaneous fluid pump fluidly connected to the at least one catheter 21. In one embodiment, the fluid pump may be fluidly connected to each catheter 21.

According to one embodiment, the system 2 further comprises at least one substance.

The present invention further relates to a method of delivering at least one substance to a vertebral body. Said method comprises the following steps:
- placing guiding means 22, such as a guiding wire, percutaneously through the skin to the final position of the bone screw in a vertebra 3;
- guiding the system 2 comprising the bone screw 1 and at least three perforated catheter 21 along the guiding means 22 to the vertebra 3 and screwing the bone screw;
- removing the guiding means 22;
- selecting at least one catheter 21 which is in a blind channel 14 of interest;

delivering at least one substance within the selected catheter 21 such that the at least one substance is discharged within the vertebral body in a chosen orientation;

optionally, implanting a fluid pump fluidly connected to the selected catheter subcutaneously.

In one embodiment, the method comprises guiding extracting means along the flexible directing means 15 to the screw head 12 and extracting the bone screw 1 and the at least three catheters 21.

The present invention further relates to a method of treating a disease, comprising delivering a therapeutically effective amount of at least one substance to a vertebral body. Said method comprises the following steps:

placing guiding means 22, such as a guiding wire, percutaneously through the skin to the final position of the bone screw in a vertebra 3;

guiding the system 2 comprising the bone screw 1 and at least three perforated catheter 21 along the guiding means 22 to the vertebra 3 and screwing the bone screw;

removing the guiding means 22;

selecting at least one catheter 21 which is in a blind channel 14 of interest;

delivering the therapeutically effective amount of at least one substance within the selected catheter 21 such that the at least one substance is discharged within the vertebral body in a chosen orientation;

optionally, implanting a fluid pump fluidly connected to the selected catheter subcutaneously.

In one embodiment, the method comprises guiding extracting means along the flexible directing means 15 to the screw head 12 and extracting the bone screw 1 and the at least three catheters 21.

In one embodiment, the disease is selected from vertebral body metastasis, vertebral tumor, acute lumbar pain, intervertebral disc spondylodiscitis or degenerative disc disease.

The present invention further relates to a method of delivering at least one substance to an intervertebral disc. Said method comprises the following steps:

placing guiding means 22, such as a guiding wire, percutaneously through the skin to the final position of the bone screw in a vertebra 3;

guiding the system 2 comprising the bone screw 1 and at least three perforated catheter 21 along the guiding means 22 to the vertebra 3 and screwing the bone screw;

removing the guiding means 22;

selecting the catheter 21 which is in the blind channel 14 directed towards the superior or the inferior end plate;

delivering at least one substance within the selected catheter 21 such that the at least one substance diffused towards respectively the superior or the inferior intervertebral disc;

optionally, implanting a fluid pump fluidly connected to the selected catheter subcutaneously.

In one embodiment, the method comprises guiding extracting means along the flexible directing means 15 to the screw head 12 and extracting the bone screw 1 and the at least three catheters 21.

The present invention further relates to a method of treating a disease, comprising delivering a therapeutically effective amount of at least one substance to an intervertebral disc. Said method comprises the following steps:

placing guiding means 22, such as a guiding wire, percutaneously through the skin to the final position of the bone screw in a vertebra 3;

guiding the system 2 comprising the bone screw 1 and at least three perforated catheter 21 along the guiding means 22 to the vertebra 3 and screwing the bone screw;

removing the guiding means 22;

selecting the catheter 21 which is in the blind channel 14 directed towards the superior or the inferior end plate;

delivering a therapeutically effective amount of at least one substance within the selected catheter 21 such that the therapeutically effective amount of the at least one substance diffused towards respectively the superior or the inferior intervertebral disc;

optionally, implanting a fluid pump fluidly connected to the selected catheter subcutaneously.

In one embodiment, the method comprises guiding extracting means along the flexible directing means 15 to the screw head 12 and extracting the bone screw 1 and the at least three catheters 21.

In one embodiment, the disease is selected from vertebral body metastasis, vertebral tumor, acute lumbar pain, intervertebral disc spondylodiscitis or degenerative disc disease.

In one embodiment, the bone screw is implanted via transpedicular approach.

In one embodiment, the system comprises a perforated catheter 21 in each blind channel 14.

In one embodiment, the system comprises a stopper 23.

According to one embodiment, the substances delivered are chemotherapeutics to treat vertebral body metastasis or vertebral tumor. According to another embodiment, the substances delivered are anesthetics to treat acute lumbar pain. According to one embodiment, the substances delivered are antibiotics to treat intervertebral disc spondylodiscitis. According to one embodiment, the substances delivered are nutrients to ensure intervertebral regeneration. According to one embodiment, the substances delivered are growth factors, non-steroid drugs, steroids, anti TNF-α to treat degenerative disc disease. According to one embodiment, the substances delivered are anesthetics to treat acute lumbar pain.

The present invention further relates to a method of treating a vertebra; said method comprising the steps of:

placing guiding means 22, such as a guiding wire, percutaneously through the skin to the final position of the bone screw in a vertebra 3;

guiding the system 2 comprising the bone screw 1 and at least one radioactive needle along the guiding means 22 to the vertebra 3 and screwing the bone screw;

removing the guiding means 22;

irradiating the vertebra 3; and guiding extracting means along the flexible directing means 15 to the screw head 12 and extracting the bone screw 1 and the at least one needle.

In one embodiment, said method is useful for treating vertebral body metastasis or vertebral tumor.

In one embodiment, the system comprises a radioactive needle in each blind channel 14.

In one embodiment, the system comprises a stopper 23.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

1—Bone screw
11—Screw body
111—Thread
112—Fenestration
12—Screw head
13—Through bore
14—Blind channel
15—Directing means
151—Braided sleeve
152—Coiled sleeve
153—Wire
2—System
21—Catheter
22—Guiding means
23—Stopper
231—O-ring
232—Guiding tube
2321—O-ring
3—Vertebra

The invention claimed is:

1. A bone screw comprising:
   a screw body comprising a proximal end, a distal end, a longitudinal axis and a thread along an exterior of all or a portion of said screw body;
   a screw head attached to the proximal end of the screw body;
   a through bore extending coaxially through said screw head and through said screw body through the proximal end and through the distal end;
   at least three blind channels angularly-disposed around the through bore; said channels extending longitudinally through said screw head and through a portion of said screw body; and each of said blind channels being configured to receive a catheter or a needle;
   a plurality of radially-disposed fenestrations; wherein a distal portion of each of said blind channels is connected to the exterior of said screw body through at least one of the fenestrations; and
   flexible directing means secured to the screw head such that an extracting tool may be guided to the screw head along said means.

2. The bone screw according to claim 1, wherein the at least three blind channels are regularly angularly disposed around the through bore.

3. The bone screw according to claim 1 wherein the at least three blind channels comprise four blind channels disposed at every 90° around the through bore.

4. The bone screw according to claim 1, wherein at least one of the at least three blind channels has a length which is different from a length of the other at least three blind channels.

5. The bone screw according to claim 1, wherein the fenestrations are elongated holes.

6. The bone screw according to claim 1, wherein the radially-disposed fenestrations are positioned between crests of adjacent thread-turns of the thread.

7. The bone screw according to claim 1, wherein one of the plurality of radially-disposed fenestrations is located at a distal end of each blind channel.

8. The bone screw according to claim 1, wherein the at least one fenestration connecting a blind channel to an exterior of the screw body is not positioned in the same transverse plane as another fenestration connecting another of the plurality of blind channels to the exterior of the screw body.

9. The bone screw according to claim 1, further comprising a radiopaque marker located within the screw body enabling angular positioning of the bone screw within a bone.

10. The bone screw according to claim 1, wherein the flexible directing means is a wire.

11. The bone screw according to claim 1, wherein the flexible directing means is hollow and configured to receive at least one catheter or at least one needle therethrough.

12. The bone screw according to claim 1, wherein the flexible directing means comprises a braided sleeve configured to receive at least one catheter or at least one needle.

13. The bone screw according to claim 1, wherein the flexible directing means comprises a coiled sleeve configured to receive at least one catheter or at least one needle.

14. The bone screw according to claim 1, wherein the thread has a lead which varies along the longitudinal axis of the screw body.

15. The bone screw according to claim 1, wherein the thread has a lead which varies along the longitudinal axis of the screw body and wherein the lead of the thread is larger in a distal portion of the screw body than in a proximal portion of the screw body.

16. A system comprising:
   a bone screw comprising:
      a screw body comprising a proximal end, a distal end, a longitudinal axis and a thread along an exterior of all or a portion of said screw body;
      a screw head attached to the proximal end of the screw body;
      a through bore extending coaxially through said screw head and through said screw body through the proximal end and through the distal end;

at least three blind channels angularly disposed around the through bore; said channels extending longitudinally through said screw head and through a portion of said screw body; and each of said blind channels being configured to receive a catheter or a needle;

a plurality of radially-disposed fenestrations; wherein a distal portion of each of said blind channels is connected to the exterior of said screw body through at least one of the fenestrations; and flexible directing means secured to the screw head such that an extracting tool may be guided to the screw head along said means; and at least one perforated catheter or at least one radioactive needle configured to be inserted into at least one of the at least three blind channels.

17. The system according to claim 16, further comprising a stopper comprising at least one opening for each perforated catheter or for each radioactive needle; wherein said stopper is configured to be inserted in the through bore of the screw head in a tight manner.

18. The system according to claim 16, further comprising a subcutaneous fluid pump fluidly connected to the at least one perforated catheter or the at least one radioactive needle.

19. A method of delivering a substance to an intervertebral disc, the intervertebral disc positioned between a superior endplate and an inferior endplate, said method comprising the following steps:

implanting via transpedicular approach at least one system comprising:

a bone screw comprising:

a screw body comprising a proximal end, a distal end, a longitudinal axis and a thread along an exterior of all or a portion of said screw body;

a screw head attached to the proximal end of the screw body;

a through bore extending coaxially through said screw head and through said screw body through the proximal end and through the distal end;

at least three blind channels angularly disposed around the through bore; said channels extending longitudinally through said screw head and through a portion of said screw body; and each of said blind channels being configured to receive a perforated catheter or a needle;

a plurality of radially-disposed fenestrations; wherein a distal portion of each of said blind channels is connected to the exterior of said screw body through at least one of the fenestrations; and flexible directing means secured to the screw head such that an extracting tool may be guided to the screw head; and at least three perforated catheters, wherein each bind channel comprises a perforated catheter therein;

selecting the perforated catheter which is in the blind channel directed towards the superior or the inferior end plate; and delivering a substance within the selected perforated catheter such that the substance diffuses towards respectively the superior or the inferior intervertebral disc.

20. The method of delivering a substance to an intervertebral disc according to claim 19, further comprising the step of guiding the extracting tool along the flexible directing means to the screw head and extracting the bone screw and the at least three perforated catheters.

21. A method of treating vertebral tumor, said method comprising the following steps:

implanting into a vertebra, via transpedicular approach, at least one system comprising:

a bone screw comprising:

a screw body comprising a proximal end, a distal end, a longitudinal axis and a thread along an exterior of all or a portion of said screw body;

a screw head attached to the proximal end of the screw body;

a through bore extending coaxially through said screw head and through said screw body through the proximal end and through the distal end;

at least three blind channels angularly disposed around the through bore; said channels extending longitudinally through said screw head and through a portion of said screw body; and each of said blind channels being configured to receive a perforated catheter or a needle;

a plurality of radially-disposed fenestrations; wherein a distal portion of each of said blind channels is connected to the exterior of said screw body through at least one fenestration; and flexible directing means secured to the screw head such that an extracting tool may be guided to the screw head; and at least one radioactive needle positioned in at least one of the at least three blind channels;

irradiating the vertebra using the at least one radioactive needle; and guiding the extracting tool along the flexible directing means to the screw head and extracting the bone screw and the at least one needle from the vertebra.

* * * * *